(12) United States Patent
Nalepa

(10) Patent No.: US 6,419,838 B1
(45) Date of Patent: Jul. 16, 2002

(54) SYNERGISTIC COMBINATIONS OF OXIDIZING AGENTS AND ALKYLAMINES FOR BIOFILM CONTROL AND DEACTIVATION

(75) Inventor: Christopher J. Nalepa, Baton Rouge, LA (US)

(73) Assignee: Albemarle Corporation, Richmond, VA (US)

(*) Notice: Subject to any disclaimer, the term of this patent is extended or adjusted under 35 U.S.C. 154(b) by 0 days.

(21) Appl. No.: 09/523,614

(22) Filed: Mar. 13, 2000

Related U.S. Application Data

(63) Continuation-in-part of application No. 09/487,743, filed on Jan. 19, 2000.

(51) Int. Cl.$^7$ .................................................. C02F 1/72
(52) U.S. Cl. ...................... 210/758; 210/764; 252/175; 422/28
(58) Field of Search ................................. 210/754, 756, 210/758, 764; 252/175; 422/28, 37

(56) References Cited

U.S. PATENT DOCUMENTS

| | | |
|---|---|---|
| 2,868,787 A | 1/1959 | Paterson et al. |
| 3,719,763 A | 3/1973 | Cline et al. |
| 4,295,971 A | 10/1981 | Khalafalla et al. |
| 5,411,666 A | 5/1995 | Hollis et al. |
| 5,817,888 A | 10/1998 | Elnagar et al. |
| 5,843,865 A | 12/1998 | Del Corral et al. |
| 5,902,699 A | 5/1999 | Jaquess et al. |
| 5,922,669 A | 7/1999 | Quebedeaux et al. |
| 6,132,628 A | * 10/2000 | Barak |

FOREIGN PATENT DOCUMENTS

| WO | WO99/13715 | 3/1999 |
|---|---|---|

OTHER PUBLICATIONS

Jon J. Kabara, et al., "Relationship of Chemical Structure and Antimicrobial Activity of Alkyl Amides and Amines"; Antimicrobial Agents and Chemotherapy, vol. 2, No. 6, Dec. 1972, p. 492–498.

M.D. Culler, et al. "Mastitis: I. In Vitro Antimicrobial Activity of Alkyl Amines Against Mastitic Bacteria"; J Dairy Sci, 1979, 62: 584–595.

Victor D. Warner, et al., "Alkylamine Salts and Amides: In Vitro Inhibition of *S mutans* 6715"; J. Dent, Res., Dec. 1977, p 1599–1602.

Hendrick J. Hueck, et al., "Bacteriostatic, Fungistatic, and Algistatic Activity fo Fatty Nitrogen Compounds"; Applied Microbiology; American Society for Microbiology; May, 1966 vol. 14, No. 3 pp. 308–319.

Ferdinand Devinsky, et al., "Cut–off Effect in Antimicrobial Activity and in Membrane Perturbation Efficiency of the Homologous Series of N,N–Dimethylalkylamine Oxides"; J. Pharm, Pharmacol, Apr. 1990, 42: 790–794

J.A. Findlay, et al.; "The Potential of Alkyl Amines as Antifouling Biocides I: Toxicity and Structure Activity Relationships"; Biofouling, 1996, vol. 9(4). pp 257–268.

A. Al–Hashem, et al.; "The Effects of Seasonal Changes on the Selection of Biocide Inhibitors for Arabian Gulf Seawater for Water Injection Purposes"; Corrosion 97, Paper No. 395.

* cited by examiner

*Primary Examiner*—Betsey Morrison Hoey
(74) *Attorney, Agent, or Firm*—Philip M. Pippenger

(57) ABSTRACT

Aqueous industrial, recreational, and/or drilling systems comprise a synergistic combination of an oxidizing agent and an alkylamine. In the synergistic combination, the MBEC of the oxidizing agent preferably is about 25%, more preferably about 50% reduced compared to the MBEC of the oxidizing agent in the absence of the alkylamine. Similarly, the MBEC of the alkylamine in the synergistic combination is about 20%, preferably about 10%, more preferably about 1%, and most preferably about 0.5% of the MBEC of the alkylamine in the absence of the oxidizing agent. Preferred alkylamines are primary fatty alkylamines, most preferably octylamine. Preferred oxidizing agents are HOCl and HOBr. The oxidizing agent preferably is maintained at a concentration sufficient to provide static control over biofilm formation with periodic addition of the alkylamine.

75 Claims, No Drawings

SYNERGISTIC COMBINATIONS OF OXIDIZING AGENTS AND ALKYLAMINES FOR BIOFILM CONTROL AND DEACTIVATION

The present application is a continuation-in-part of co-pending application, Ser. No. 09/487,743, filed Jan. 19, 2000.

FIELD OF THE INVENTION

The invention relates to synergistic combinations of oxidizing and non-oxidizing agents for static control and deactivation of biofilms on surfaces in a variety of aqueous systems, including but not necessarily limited to recreational and industrial water systems. The synergistic combination also may be used to prevent the corrosion of metal equipment when used in aqueous drilling systems. More particularly, the invention relates to synergistic combinations of alkylamines and oxidizing agents for such purposes.

BACKGROUND OF THE INVENTION

Biological fouling is a serious economic problem in both industrial and recreational water systems. Biological fouling is the buildup of a "biofilm" on the surfaces that come into contact with the water in the system. A "biofilm" is the buildup of layers of microorganisms and/or extracellular substances and the dirt and/or debris that becomes trapped in that buildup. Bacteria, fungi, yeasts, diatoms and protozoa are only some of the organisms that cause the buildup of a biofilm.

In recreational waters, biofilms tend to be "slimey" to the touch, and can create a health hazard. In industrial waters, biofouling can interfere with industrial processes, lowering the efficiency of the process, wasting energy, and reducing product quality. In drilling systems, biofouling contributes to the corrosion of expensive drilling equipment.

Biofilm problems are encountered frequently in cooling water systems used in power-generating plants, refineries, chemical plants, and air conditioning systems. Cooling water systems commonly are contaminated with airborne organisms entrained by air/water contact in cooling towers as well as waterborne organisms from the system's makeup water supply. The water in such systems generally is an excellent growth medium for these organisms. If not controlled, the biofilm that results from such growth can plug towers, block pipelines, and coat heat transfer surfaces with layers of slime, thereby preventing proper operation and reducing the efficiency of the affected equipment.

Biofilms traditionally are controlled using oxidizing agents, which typically are based on chlorine or bromine. Oxidizing systems are effective to control biofilms, but such systems also can corrode valuable metal equipment and may irritate delicate and/or sensitive skin. A system that would require treatment with a minimal amount of an oxidizing agent would be desirable.

Non-oxidizing agents are available to control biofilms, and should avoid the foregoing problems; however, oxidizing biocides tend to be much more effective than non-oxidizing biocides at deactivating a biofilm. Biofilms also tend to require exposure to much higher doses of non-oxidizing agents for much longer periods of time than the dosage and time required to kill microorganisms in a suspension. As a result, non-oxidizing agents tend to be much more expensive to use as biofilm deactivation agents than oxidizing agents.

The current trend is towards using continuous levels of oxidizing biocides to maintain clean water system surfaces and to decrease the risk of contamination by *Legionella pneumophila*, the bacteria responsible for Legionnaire's disease. A continuous need exists for means to minimize the quantity of an agent required to deactivate a biofilm, whether the agent is an oxidizing agent or a non-oxidizing agent.

SUMMARY OF THE INVENTION

The invention provides an aqueous system comprising a synergistic minimum biofilm eradication concentration ("MBEC") of a synergistic combination comprising an amount of an oxidizing agent and a quantity of an alkylamine. The oxidizing agent has an "oxidizing MBEC" in the absence of the alkylamine and the alkylamine has an "alkylamine MBEC" in the absence of the oxidizing agent. The synergistic MBEC comprises a reduction in at least one of an MBEC selected from the group consisting of said oxidizing MBEC and said alkylamine MBEC.

DETAILED DESCRIPTION OF THE INVENTION

The invention provides a synergistic combination useful as a biocide and/or as a corrosion inhibitor in a wide variety of aqueous systems. The term "aqueous system" includes, but is not necessarily limited to recreational systems, industrial systems, and aqueous base drilling systems. Suitable industrial systems include, but are not necessarily limited to cooling water systems used in power-generating plants, refineries, chemical plants, air conditioning systems, process systems used to manufacture pulp, paper, paperboard, and textiles, particularly water laid nonwoven fabrics.

The synergistic combination comprises an alkylamine having an "alkylamine MBEC" and an oxidizing agent having an "oxidizing MBEC." The synergistic combination reduces the quantity of at least one of these values to achieve a "synergistic MBEC."

The "MBEC"

The MBEC is a valuable measurement for determining whether the quantity of given agent that will be required to eradicate a biofilm will be economically and environmentally feasible. The MBEC test was developed by the University of Calgary to evaluate the efficacy of antibiotics and biocides towards biofilms. H. Ceri, et. al., "The MBEC Test: A New In Vitro Assay Allowing Rapid Screening for Antibiotic Sensitivity of Biofilm", *Proceedings of the ASM*, 98, p 525 (1998). Ceri, et. al., "Antifungal and Biocide Susceptibility testing of Candida Biofilms using the MBEC Device," Proceedings of the Interscience Conference on Antimicrobial Agents and Chemotherapy, vol. 38, p. 495 (1998); H. Ceri, et. al., "The Calgary Biofilm Device: A New Technology for the Rapid Determination of Antibiotic Susceptibility of Bacterial Biofilms," *Journal of Clinical Microbiology* 37 (1999) 1771–1776. The exclusive license for the MBEC technique is believed to be held by MBEC Biofilm Technologies, 665-8th Street S.W., Calgary, Alberta T2P 4H5 Canada.

The MBEC technique consists of growing identical 24-hour biofilms on 96 pegs arrayed in 12 rows and 8 columns. The biofilms then are challenged with decreasing concentrations of selected antibiotics and/or biocides. After a certain challenge time (generally one hour), the biofilms are placed in 96 individual wells of growth media and ultrasonicated to deactivate any surviving organisms. After culturing overnight, the wells are checked for turbidity. Clear, transparent wells indicate complete deactivation of the biofilm. Conversely, turbidity ("growth") indicates lack of complete deactivation of the biofilm.

The minimum biofilm eradication concentration (MBEC) is defined as the minimum concentration of an agent that completely deactivates biofilm bacteria. The MBEC technique provides a potentially powerful and reproducible tool to study the efficacy of biocides and additives towards biofilm deactivation. Unless otherwise indicated, the biofilms used in the examples below consisted of a pure culture of *Pseudomonas aeruginosa* (ATCC 15442). The reason for this is that *Pseudomonas aeruginosa* often represents the major biofilm component in industrial and recreational water systems. J. W. Costerton and H. Anwar, "*Pseudomonas aeruginosa*: The Microbe and Pathogen", in "*Pseudomonas aeruginosa* Infections and Treatment", A. L. Baltch and R. P. Smith (eds.), Marcel Dekker, N.Y., 1994. In addition, *Pseudomonas aeruginosa* is a gram-negative bacteria. Gram-negative bacteria tend to be more difficult to kill than gram-positive bacteria. In other words, if an agent is effective against *Pseudomonas aeruginosa*, then persons of ordinary skill in the art would find it reasonable to predict that the agent also would be effective against other microorganisms found in biofilms.

The Oxidizing Agent

A wide variety of oxidizing agents are known to control biofilm growth. Any of such oxidizing agents are suitable for use in the synergistic combination as long as they meet one of the synergistic parameters defined herein. Preferred oxidizing agents are capable of supplying a $Cl^+$ ion or a $Br^+$ ion. Examples include, but are not necessarily limited to HOBr and salts thereof, HOCl and salts thereof, and organic halogen carriers wherein the halogen is selected from the group consisting of bromine and chlorine.

Examples of suitable organic halogen carriers are described in U.S. Pat. No. 2,868,787, incorporated herein by reference, and include, but are not necessarily limited to halogenating agents containing at least one N-halogen radical in which the halogen atom is loosely bound to the nitrogen atom and is readily available for chemical reaction. Such compounds include, but are not necessarily limited to N-bromo succinimide, N-bromo phthalimide, N-bromocyanuric acids, N-bromo melamines, N,N-dibromo-5 substituted hydantoins, N-bromo-toluene-sulfonamide, N-bromo-3a,6a-substituted glycolurils, N-bromo-5 substituted hydantoins, N-bromo-toluene-sulfonamide, N-bromo-3a,6a-substituted glycolurils, N-bromo-5-substituted hydantoins, N-bromo-toluene-sulfonamide, N-bromo-3a,6a-substituted-glycolurils, N-bromo-5-substituted barbiturates and the like are contemplated as products which may be prepared by this process. In addition, one also may prepare the mixed dihalo-(N-bromo-N-chloro) compounds where more than a single nitrogen atom is in the carrier molecule, such as for example, N-chloro-N-bromo-5 substituted hydantoin. Preferred organic halogen carriers are N-cyclic imides and are represented by the hydantoins, succinimide, phthalimide, cyanuric acid, the glycolurils, and the like. Preferred oxidizing agents are inorganic oxidizing agents, most preferably HOBr and salts thereof and HOCl and salts thereof. Other preferred oxidizing agents are stabilized bromine systems, such as those described in U.S. Pat. No. 5,795,487 and WO9962339, incorporated herein by reference.

One way to define suitable alkylamines and oxidizing agents for use in the invention is to compare the reduction in concentration of each component required to produce an MBEC for the synergistic combination compared to the concentration of the same component required to achieve an MBEC when the component is used in the absence of the other component.

The MBEC of HOBr is known to be about 2.5 ppm. The MBEC of HOCl is known to be about 3.8 ppm. In a preferred synergistic combination, the concentration of one of either the oxidizing agent or the alkylamine required to produce an MBEC for the combination is less than the concentration of that component in the absence of the other agent. In a preferred embodiment, the MBEC for the oxidizing agent is reduced by about 25% or more, most preferably by about 50% or more. Where the oxidizing agent is HOCl, the synergistic combination preferably reduces the required concentration of the HOCl to about 3.0 ppm or less, preferably to about 2 ppm or less. Where the oxidizing agent is HOBr, the synergistic combination preferably reduces the required concentration of the HOBr to about 2 ppm or less, more preferably to about 1.25 ppm or less. A most preferred alkylamine is octylamine, which (a) reduced the MBEC of HOBr from 2.5 ppm to about 1.25 ppm, and (b) reduced the MBEC of HOCl from about 3.8 ppm to about 1.9 ppm.

The Alkylamine

A variety of alkylamines will produce a synergistic combination when mixed with solution of a suitable oxidizing agent. Suitable alkylamines include, but are not necessarily limited to primary fatty alkyl amines, alkyl-substituted primary fatty alkylamines, alkyldimethylamines, and dialkylmethylamines. Preferred alkylamines are primary fatty alkylamines and alkyl-substituted primary fatty alkylamines, most preferably primary fatty alkylamines, with a most preferred alkylamine being octylamine.

Suitable alkylamines are commercially available from Aldrich Chemicals Ltd. or Sigma Chemical Company. Dodecylamine also is available from Akzo, Nobel Chemicals Inc. Suitable alkylamines also may be made by persons of ordinary skill in the art using known procedures, such as those described in R. Morrison and R. Boyd. *Organic Chemistry* ($5^{th}$ Ed. 1987) §§ 26.11–26.13, pp. 945–948, incorporated herein by reference.

In systems in which an alkylamine is a preferred biofilm deactivation agent, the oxidizing agent is used to decrease the amount of the alkylamine required to produce an MBEC for the combination. Preferably, the oxidizing agent reduces the required quantity of the alkylamine to about 20% or less, more preferably to about 10% or less, even more preferably to about 1% or less, and most preferably to about 0.5% or less of its MBEC in the absence of the oxidizing agent.

In a preferred embodiment, the oxidizing agent is maintained at a concentration effective to maintain static control of the system, and the alkylamine periodically is added to increase the efficacy of the oxidizing agent, or to reduce the MBEC of the oxidizing agent. In this embodiment, the quantity of the alkylamine required to reduce the MBEC of the oxidizing agent is about 20% or less, preferably about 10% or less, more preferably about 1% or less, and most preferably about 0.5% or less of the MBEC of the alkylamine. A preferred embodiment uses less than 25 ppm, preferably from about 5 to about 25 ppm, most preferably about 5 ppm of the alkylamine.

The reduced synergistic MBEC for the components in the synergistic combination results in a proportionate reduction in the quantity of both the oxidizing agent and the relatively expensive alkylamine that is required to treat the aqueous system. As a general rule of thumb, about 1 pound of a biofilm treatment agent will result in 10 ppm of actives in a 12,000 gallon aqueous system. If used alone to treat an aqueous system, 40 pounds of octylamine (MBEC, 400 ppm) would be required to achieve an MBEC of 400 ppm of the octylamine in the system. In contrast, when combined with a synergistic oxidizing agent, even at one-half the concentration of the oxidizing agent, only about 0.5 to about 2.5 pounds of the octylamine is required.

One way to define suitable alkylamines for use in the synergistic combination herein is by their octanol/water partition coefficient. The octanol/water partition coefficient, or "$K_{ow}$", is defined as the ratio of the concentration of a given compound found in the octanol phase to the concentration of the compound found in the water phase under known conditions. The octanol/water partition coefficient, or "$K_{ow}$", usually is expressed as a logarithm. A log$K_{ow}$ of 3.0 means that the compound is 1000 times more soluble in octanol than in water. Persons of ordinary skill in the art understand that compounds with relatively high $K_{ow}$ values have a tendency to accumulate in the tissue of living organisms. However, if the $K_{ow}$ value is too high, the compound may have limited aqueous solubility. Octanol was chosen to measure the tendency of a compound to bioaccumulate because octanol "mimics" the lipids found in living organisms and thus forms the basis for a simple assay for measuring potential biological interactions.

The octanol/water partition coefficient of a given alkylamine may be measured or calculated using a variety of known methods. The values in the following Tables were calculated using the KowWIN program of the Environmental Science Center of Syracuse Research Corporation (http://esc.syrres.com/esc.htm ). See also Meylan, W. M. and P. H. Howard. Atom/fragment contribution method for estimating octanol-water partition coefficients. *J Pharm. Sci*. 84: 83–92 (1995), incorporated herein by reference. Experimentally determined values are given for some alkylamines in N. Bodor, Z. Gabanyi, and C-K. Wang, Journal of the American Chemical Society, 111, 3783–3786 (1989), incorporated herein by reference.

The KowWIN program estimates the log octanol/water partition coefficient (log P) of organic chemicals using the atom/fragment contribution method. Based on the results of these calculations, persons of ordinary skill in the art would expect that, when combined with a solution of a suitable quantity of a synergistic oxidizing agent, alkylamines that form a synergistic combination will be those with a calculated octanol/water partition coefficient of from about 2 to about 6, preferably from about 2 to about 5, more preferably from about 2.0 to about 3.0, and most preferably from about 2.5 to about 3.

The following are the calculated log$K_{ow}$ values (calculated using the KowWIN program) and published experimentally determined log$K_{ow}$ values (id.) for the following alkylamines:

| Alkylamines | | |
|---|---|---|
| Compound | log$K_{ow}$ calculated | log$K_{ow}$ experimental |
| 1-Butylamine | 0.97 | |
| 1-Pentylamine | 1.49 | |
| 1-Hexylamine | 1.82 | 2.06 (1) |
| 1-Heptylamine | 2.31 | |
| 1-Octylamine | 2.8 | 2.9 (1) |
| 1-Nonylamine | 3.29 | |
| 1-Decylamine | 3.78 | |
| 1-Undecylamine | 4.27 | |
| 1-Dodecylamine | 4.76 | |
| 1-Tridecylamine | 5.25 | |
| 1-Tetradecylamine | 5.75 | |
| 1-Pentadecylamine | 6.24 | |
| 1-Hexadecylamine | 6.73 | |

| Alkyldimethylamines (ADMAs) | | |
|---|---|---|
| Compound | log$K_{ow}$ calculated | log$K_{ow}$ experimental |
| N,N-Dimethylbutylamine | 1.51 | 1.7(1) |
| N,N-Dimethylpentylamine | 2 | |
| N,N-Dimethylhexylamine | 2.49 | |
| N,N-Dimethylheptylamine | 2.99 | |
| N,N-Dimethyloctylamine | 3.48 | |
| N,N-Dimethylnonylamine | 3.97 | |
| N,N-Dimethyldecylamine | 4.46 | |
| N,N-Dimethylundecylamine | 4.95 | |
| N,N-Dimethyldodecylamine | 5.44 | |
| N,N-Dimethyltridecylamine | 5.93 | |
| N,N-Dimethyltetradecylamine | 6.42 | |

1. Hansh and Leo, 1985

| Dialkylamines | | |
|---|---|---|
| Compound | log$K_{ow}$ calculated | log$K_{ow}$ experimental |
| N,N-Dibutylamine | 2.77 | 2.83(1) |
| N,N-Dipentylamine | 3.76 | |
| N,N-Dihexylamine | 4.74 | |
| N,N-Diheptylamine | 5.72 | |
| N,N-Dioctylamine | 6.7 | |

1. Hansh and Leo, 1985

| Alkyldimethylbenzylammonium Chlorides (ADBACS) | | |
|---|---|---|
| Compound | log$K_{ow}$ calculated | log$K_{ow}$ experimental |
| Octyldimethylbenzylammonium chloride | 0.96 | |
| Nonyldimethylbenzylammonium chloride | 1.45 | |
| Decyldimethylbenzylammonium chloride | 1.95 | |
| Undecyldimethylbenzylammonium chloride | 2.44 | |
| Dodecyldimethylbenzylammonium chloride | 2.93 | |
| Tridecyldimethylbenzylammonium chloride | 3.42 | |
| Tetradecyldimethylbenzylammonium chloride | 3.91 | |
| Pentadecyldimethylbenzylammonium chloride | 4.4 | |
| Hexadecyldimethylbenzylammonium chloride | 4.89 | |
| Heptadecyldimethylbenzylammonium chloride | 5.38 | |
| Octadecyldimethylbenzylammonium chloride | 5.87 | |
| Nonadecyldimethylbenzylammonium chloride | 6.37 | |
| Eicosyldimethylbenzylammonium chloride | 6.86 | |

| Dialkyldimethylammonium Chlorides (DIDACs) | | |
|---|---|---|
| Compound | log$K_{ow}$ calculated | log$K_{ow}$ experimental |
| Dihexyldimethylammonium chloride | 0.73 | |
| Diheptyldimethylammonium chloride | 1.71 | |
| Dioctyldimethylammonium chloride | 2.69 | |
| Dinonyldimethylammonium chloride | 3.68 | |
| Didecyldimethylammonium chloride | 4.66 | |
| Diundecyldimethylammonium chloride | 5.64 | |
| Didodecyldimethylammonium chloride | 6.62 | |

Based on the foregoing calculated octanol/water partition coefficients, preferred alkylamines are unsubstituted and alkyl substituted primary fatty alkylamines comprising a primary alkyl group having from about 7 to about 15, more preferably from about 7 to about 12, even more preferably from about 7 to about 8 carbon atoms, and most preferably about 8 carbon atoms, and comprising substituent alkyl groups having from about 0 to about 6 carbon atoms, preferably from about 0 to about 4 carbon atoms, more preferably from about 0 to about 1 carbon atom, most preferably 0 carbon atoms. Examples of substituted primary fatty alkylamines include alkyldimethylamines comprising a primary alkyl group having from about 5 to about 13 carbon atoms, preferably from about 5 to about 11 carbon atoms, more preferably from about 5 to about 7 carbon atoms, and most preferably from about 6 to about 7 carbon atoms. Also suitable according to their calculated octanol water partition coefficients are dialkylamines comprising alkyl groups having from about 4 to about 7 carbon atoms, preferably from about 4 to about 6 carbon atoms, more preferably about 4 carbon atoms, alkyldimethylbenzylammonium chlorides comprising an alkyl group having from about 10 to about 18 carbon atoms, preferably from about 11 to about 16 carbon atoms, more preferably from about 11 to about 12 carbon atoms, and most preferably about 12 carbon atoms, and dialkyldimethylammonium chlorides comprising alkyl groups having from about 8 to about 11 carbon atoms, preferably from about 8 to about 10 carbon atoms, most preferably 8 carbon atoms.

The invention will be better understood with reference to the following Example, which is illustrative only and should not be construed as limiting the invention to a specific embodiment. The procedures used in the example were as follows:

Section A—Preparation and Activity Testing of Biocide Formulations

Preparation of Synthetic Water

Synthetic water (SW) was prepared by adding 0.22 g $CaCl_2$, 0.168 g $NaHCO_3$, and 0.014 g NaCl to 1 L of deionized, distilled water (DDW). The mixture was sterilized by filtration through a 0.2 $\mu m$ filter. The pH of this solution was 7.9 to 8.1 units and afforded a water containing 200 ppm Ca hardness (as $CaCO_3$), 150 ppm of alkalinity (as $CaCO_3$), and 150 ppm of chloride.

Preparation of 400 ppm Octylamine Solution

The stock 2500 ppm solution of octylamine in SW was prepared by diluting 0.05 g octylamine to 20.0 g in SW. A cloudy mixture resulted. To help solubilize the amine, 5 drops of 4% aq. HCl was added. This afforded a slightly cloudy solution with some foam which was stirred continuously prior to diluting 3.2 g of stock to 20.0 g with SW.

Preparation of 100 ppm Dodecylamine Solution

Stock 2500 ppm dodecylamine was prepared by diluting 0.038 g to 15.2 g in SW. About 5 drops of 4% aq. HCl was added and the mixture was heated and stirred to aid dissolution (dodecylamine is a solid at room temperature). This yielded a pearlescent suspension which was continually stirred prior to diluting 0.80 g of the stock solution to 20.0 g with SW.

Section B—Microbiological Procedures

Biofim Preparation and Biocide Challenge *Pseudomonas aeruginosa* (ATCC 15442) biofilms were prepared on the 96 pegs of the MBEC plate by aerobic incubation in simple salts medium with 0.1% glucose (24 hours, 35° C.). The pegs were rinsed in synthetic water (SW) and then challenged by the biocide for one hour. Following the biocide challenge, the pegs were rinsed twice with SW and then sonicated into Mueller-Hinton broth (225 $\mu L$ per well). The broth was then incubated for 18 hours at 35° C.

Determination of Minimum Biofilm Deactivation Concentration

After the 18 hour incubation period, the recovery wells were checked for turbidity. Clear, transparent wells indicated complete deactivation of the biofilm. Conversely, turbidity indicated the lack of complete deactivation of the biofilm. The minimum biofilm deactivation concentration (MBEC) is defined as the minimum concentration of agent which results in complete deactivation of the biofilm. MBEC endpoints were unambiguously determined by absorbance at 650 nm. using UV visible spectroscopy. An absorbance>0.100 was considered a positive indication of growth.

MBEC values for duplicate runs on the same plate were typically the same. In cases where duplicate runs were not the same, the difference almost always represented just one 50% dilution in biocide concentration or one well of the 96 well plate.

Control Data

Formulations in all of this work were run in duplicate together with suitable controls. Various microbiological controls and checks also were run to assure the integrity of the experimental methods employed. For example, initial and final concentrations of inocula used to grow the biofilms (McFarland=1.0) were checked using serial plating.

In addition to the above work, 12 peg sites (representing row 8 on each MBEC plate) also were used for various control purposes. The biocide plates contained just synthetic water (no biocide) in row 8. Sterility controls were run by removing MBEC pegs in row 8, columns 1–3 prior to growth of the biofilm. These were then taken through the entire procedure. Since no biofilm could grow (pegs removed), no turbidity (indicates viable bacteria) should be observed. 24-Hour biofilm controls were determined by removing pegs 4–6, row 8 immediately after 24-hour biofilm growth. The pegs were sonicated in saline to remove the biofilm and serially plated. Biocide challenge controls were determined by removing pegs 7–9, row 8 following biocide challenge and treating the pegs as 4–6 above. Turbidity controls were run by taking pegs 10–12 through the entire MBEC procedure. Since the biofilms saw no biocide (only synthetic water), these samples should turn turbid.

The control data indicated no unusual circumstances or contamination during these experiments. The average biofilm concentration on the pegs was $1.0 \times 10^7$ CFUs/ peg.

EXAMPLE

In this study, a comparison was made of the activity of: (1) octylamine and dodecylamine, alone; (2) certain oxidizing agents having known MBEC's, alone; and, (3) combinations of the amines and the oxidizing agent. Octylamine and dodecylamine were chosen because the calculated octanol water partition coefficient for each of these alkylamines is from about 2 to about 5 (octylamine, 2.8; dodecylamine, 4.76). Based on their calculated octanol water partition coefficient, each of these alkylamines were expected to produce a synergistic combination with a suitable oxidizing agent. The MBEC of the alkylamines in the absence of an oxidizing agent were as follows, in duplicate readings: octylamine, 400 ppm; dodecylamine, 25 ppm.

HOBr and HOCl were used to test for synergistic effect. The MBEC of HOBr is known to be about 2.5 ppm. The MBEC of HOCl is known to be about 3.8. 300 $\mu l$ of the Biocide Formulation was added to each well. The alkylamines were tested alone in aqueous solution. Each of the combinations contained 5 ppm of the listed amine in aqueous solutions of either HOCl or HOBr.

Effect of Fatty Amines on Activity of HOCl and HOBr

| Biocide Formulation | MBEC, ppm | MBEC, avg. |
|---|---|---|
| n-octylamine | 400, 400 | 400 |
| n-dodecylamine | 25, 25 | 25 |
| HOCl + n-octylamine | 2.5, 2.5 | 2.5 (a) |
| HOBr + n-octylamine | 1.2, 1.2 | 1.2 |
| HOCl + n-dodecylamine | 1.2, 2.5 | 1.9 (b) |
| HOBr + n-dodecylamine | 5, 5 | 5 |

(a) Growth at 5 ppm $Cl_2$ level in one case
(b) Growth at 2.5 ppm $Cl_2$ level in one case and 5 ppm $Cl_2$ level in the other.

a. Growth at 5 ppm $Cl_2$ level in one case
b. Growth at 2.5 ppm $Cl_2$ level in one case and 5 ppm $Cl_2$ level in the other.

As predicted by their octanol water partition coefficients, the combinations were synergistic combinations. HOCl combined with 5 ppm of either dodecylamine or octylamine produced a synergistic combination in which the required concentration of the oxidizing agent consistently was reduced by at least about 50%. However, when HOBr was combined with dodecylamine, the amount of the oxidizing agent required to achieve MBEC of the combination actually increased to greater than the MBEC of the oxidizing agent, alone.

Based on these results, suitable combinations include octylamine and dodecylamine combined with HOCl, and octylamine with HOBr. A most preferred synergistic combination is from about 5 ppm to about 25 ppm, preferably about 5 ppm of octylamine and HOBr.

Persons of ordinary skill in the art will recognize that many modifications may be made to the present invention without departing from the spirit and scope of the invention. The embodiment described herein is meant to be illustrative only and should not be taken as limiting the invention, which is defined in the following claims.

I claim:

1. An aqueous system which comprises a combination comprised of an oxidizing agent and an alkylamine in proportions such that the minimum biofilm eradication concentration ("MBEC") of the combination is less than the MBEC of (a) and (b), wherein (a) is the MBEC of the oxidizing agent when used individually in the system and (b) is the MBEC of the alkylamine when used individually in the system.

2. The system of claim 1 wherein the MBEC of said combination is about 25% or less of the MBEC of (a).

3. The system of claim 2 wherein the MBEC of said combination is about 20% or less of the MBEC of (t).

4. The aqueous system of claim 3 wherein said alkylamine is a primary alkylamine having from about 7 to about 15 carbon atoms.

5. The system of claim 2 wherein the MBEC of said combination is about 10% or less of the MBEC of (b).

6. The aqueous system of claim 5 wherein said alkylamine is octylamine.

7. The aqueous system of claim 5 wherein said oxidizing agent is selected from the group consisting of HOBr and salts thereof, HOCl and salts thereof, and combinations thereof.

8. The system of claim 2 wherein the MBEC of said combination is about 1% or less of the MBEC of (b).

9. The aqueous system of claim 8 wherein said alkylamine is octylamine.

10. The aqueous system of claim 8 wherein said oxidizing agent is selected from the group consisting of HOBr and salts thereof, HOCl and salts thereof, and combinations thereof.

11. The system of claim 2 wherein the MBEC of said combination is about 0.5% or less of the MBEC of (b).

12. The system of claim 2 wherein said alkylamine is used in an amount of less than about 25 ppm.

13. The system of claim 2 wherein said alkylaniine is used in an amount of about 5 to about 25 ppm.

14. The system of claim 2 wherein said alkylamine is used in an amount of about 5 ppm or less.

15. The system of claim 1 wherein the MBEC of said combination is about 50% or less of the MBEC of (a).

16. The system of claim 15 wherein the MBEC of said combination is about 20% or less of the MBEC of (b).

17. The system of claim 15 wherein the MBEC of said combination is about 10% or less of the MBEC of (b).

18. The system of claim 15 wherein the MBEC of said combination is about 1% or less of the MBEC of (b).

19. The system of claim 15 wherein the MBEC of said combination is about 0.5% or less of the MBEC of (b).

20. The system of claim 15 wherein said alkylamine is used in an amount of less than about 25 ppm.

21. The system of claim 15 wherein said alkylamine is used in an amount of about 5 to about 25 ppm.

22. The system of claim 15 wherein said alkylamine is used in an amount of about 5 ppm or less.

23. The aqueous system of claim 15 wherein said alkylamine is a primary alkylamine having from about 7 to about 15 carbon atoms.

24. The aqueous system of claim 15 wherein said alkylamine is octylamine.

25. The aqueous system of claim 15 wherein said oxidizing agent is selected from the group consisting of HOBr and salts thereof, HOCl and salts thereof, and combinations thereof.

26. The system of claim 1 wherein the MBEC of said combination is about 20% or less of the MBEC of (b).

27. The aqueous system of claim 26 wherein said alkylamine is a primary alkylamine having from about 7 to about 15 carbon atoms.

28. The system of claim 1 wherein the MBEC of said combination is about 10% or less of the MBEC of (b).

29. The system of claim 1 wherein the MBEC of said combination is about 1% or less of the MBEC of (b).

30. The aqueous system of claim 29 wherein said oxidizing agent is selected from the group consisting of HOBr and salts thereof, HOCl and salts thereof, and combinations thereof.

31. The aqueous system of claim 29 wherein said alkylamine is octylamine.

32. The system of claim 1 wherein the MBEC of said combination is about 0.5% or less of the MBEC of (b).

33. The aqueous system of claim 32 wherein said alkylamine is a primary alkylamine having from about 7 to about 15 carbon atoms.

34. The system of claim 1 wherein said alkylamine is used in an amount of about 25 ppm or less.

35. The system of claim 1 wherein said alkylamine is used in an amount of about 5 to about 25 ppm.

36. The system of claim 1 wherein said alkylamine is used in an amount of about 5 ppm or less.

37. The aqueous system of claim 1 wherein said alkylamine is a primary alkylamine having from about 7 to about 15 carbon atoms.

38. The aqueous system of claim 1 wherein said alkylamine is octylamine.

39. The aqueous system of claim 1 wherein said oxidizing agent is selected from the group consisting of HOBr and salts thereof, HOCl and salts thereof, and combinations thereof.

40. An aqueous system comprising a synergistic combination comprising an alkylamine and HOCl, wherein HOCl is present in a concentration of 3.8 ppm or less.

41. The aqueous system of claim 40 wherein said concentration of said HOCl is 3 ppm or less.

42. The aqueous system of claim 40 wherein said concentration of said HOCl is 2 ppm or less.

43. The aqueous system of claim 42 wherein said alkylamine is octylamine.

44. An aqueous system comprising a synergistic combination comprising an alkylamine and HOBr, wherein HOBr is present in a concentration of 2.5 ppm or less.

45. The aqueous system of claim 44 wherein said concentration of said HOBr is 2 ppm or less.

46. The aqueous system of claim 45 wherein said alkylamine is octylamine.

47. The aqueous system of claim 44 wherein said concentration of said HOBr is 1.25 ppm or less.

48. The aqueous system of claim 47 wherein said alkylamine is octylamine.

49. An aqueous system comprising an MBEC of a synergistic combination comprising:
 a quantity of octylamine; and,
 an amount of an oxidizing agent selected from the group consisting of HOBr and salts thereof, HOCl and salts thereof, and combinations thereof.

50. The aqueous system of claim 49 wherein said quantity is less than about 25 ppm.

51. The aqueous system of claim 49 wherein said quantity is from about 5 ppm to about 25 ppm.

52. The aqueous system of claim 49 wherein said quantity is about 5 ppm or less.

53. An aqueous system comprising an MBEC of a synergistic combination comprising:
 an amount of an oxidizing agent having an oxidizing MBEC; and
 a quantity of an alkylamine having an alkylamine MBEC and having an octanol/water partition coefficient of from about 2 to about 6.

54. The aqueous system of claim 53 wherein said octanol/water partition coefficient is from about 2 to about 5.

55. The aqueous system of claim 54 wherein said oxidizing agent is selected from the group consisting of HOBr and salts thereof, HOCl and salts thereof, and combinations thereof.

56. The aqueous system of claim 53 wherein said octanol/water partition coefficient is from about 2 to about 3.

57. The aqueous system of claim 56 wherein said oxidizing agent is selected from the group consisting of HOBr, salts thereof and HOCl and salts thereof, and combinations thereof.

58. The aqueous system of claim 53 wherein said octanol/water partition coefficient is from about 2.5 to about 3.

59. The aqueous system of claim 58 wherein said oxidizing agent is selected from the group consisting of HOBr, salts thereof and HOCl and salts thereof, and combinations thereof.

60. The aqueous system of claim 53 wherein said oxidizing agent is selected from the group consisting of HOBr and salts thereof, HOCl and salts thereof, and combinations thereof.

61. A method of treating an aqueous system, which method comprises: maintaining in said aqueous system a concentration of an oxidizing agent effective to maintain static control over biofilm formation in said system; and periodically adding to said aqueous system a quantity of an alkylamine that is synergistic with the oxidizing agent.

62. The method of claim 61 wherein said concentration of said oxidizing agent is about 25% or less than the MBEC of the oxidizing agent when used individually.

63. The method of claim 62 wherein said quantity of said alkylamine is about 10% or less of the MBEC of the alkylamine when used individually.

64. The method of claim 62 wherein said quantity of said alkylamine is about 1% or less of the MBEC of the alkylamine when used individually.

65. The method of claim 62 wherein said quantity of said alkylamine is about 20% or less of the MBEC of the alkylamine when used individually.

66. The method of claim 62 wherein said quantity of said alkylamine is about 0.5% or less of the MBEC of the alkylamine when used individually.

67. The method of claim 61 wherein said concentration of said oxidizing agent is about 50% or less than the MBEC of the oxidizing agent when used individually.

68. The method of claim 67 wherein said quantity of said alkylamine is about 10% or less of the MBEC of the alkylamine when used individually.

69. The method of claim 67 wherein said quantity of said alkylamine is about 1% or less of the MBEC of the alkylamine when used individually.

70. The method of claim 67 wherein said quantity of said alkylamine is about 20% or less of the MBEC of the alkylamine when used individually.

71. The method of claim 67 wherein said quantity of said alkylamine is about 0.5% or less of the MBEC of the alkylamine when used individually.

72. The method of claim 61 wherein said quantity of said alkylamine is about 10% or less of the MBEC of the alkylamine when used individually.

73. The method of claim 61 wherein said quantity of said alkylamine is about 1% or less of the MBEC of the alkylamine when used individually.

74. The method of claim 61 wherein said quantity of said alkylamine is about 20% or less of the MBEC of the alkylamine when used individually.

75. The method of claim 61 wherein said quantity of said alkylamine is about 0.5% or less of the MBEC of the alkylamine when used individually.

* * * * *